United States Patent
Giesen et al.

(12)

(10) Patent No.: US 6,447,999 B1
(45) Date of Patent: Sep. 10, 2002

(54) DETERMINATION OF ANALYTES BY MEANS OF TWO MARKERS

(75) Inventors: Ursula Giesen, Weilheim; Peter Wenzig, München; Günter Ziegler, Polling; Kurt Weindel, Wielenbach, all of (DE)

(73) Assignee: Roche Diagnostics GmbH, Mannheim (DE)

( * ) Notice: Subject to any disclaimer, the term of this patent is extended or adjusted under 35 U.S.C. 154(b) by 0 days.

(21) Appl. No.: 09/147,472

(22) PCT Filed: Jul. 2, 1997

(86) PCT No.: PCT/EP97/03480
§ 371 (c)(1),
(2), (4) Date: Feb. 16, 1999

(87) PCT Pub. No.: WO98/01578
PCT Pub. Date: Jan. 15, 1998

(30) Foreign Application Priority Data

Jul. 6, 1996 (DE) .......................................... 196 27 290

(51) Int. Cl.[7] .......................... C12Q 1/68; G01N 33/53; G01N 33/00; C12P 19/34; C07H 21/04
(52) U.S. Cl. ............................ 435/6; 435/7.1; 435/91.1; 435/91.2; 436/94; 536/24.3; 536/24.33
(58) Field of Search ........................... 435/6, 7.1, 283.1, 435/287.2, 292.1, 808, 975, 94, 91.1, 91.2; 436/164, 172; 536/23.1, 25.3, 24.33, 24.3

(56) References Cited

U.S. PATENT DOCUMENTS 5,278,043 A * 1/1994 Bannwarth et al. ........ 535/23.1
5,538,871 A * 7/1996 Nuovo et al. ............... 435/91.2
5,663,047 A * 9/1997 Obata et al. .................... 435/6

OTHER PUBLICATIONS

Maslanka et al., Molecular analysis of T cell repertoires. Spectratypes generated by multiplex polymerase chain reaction and evaluated by radioactivity or fluorescence. Hum. Immunol. 44, 28–34, Sep. 1995.*
Cardullo et al., Detection of nucleic acid hybridization by nonradiative fluorescence resonance energy transfer. Proc. Natl. Acad. Sci. USA 85, 8790–8794, Dec. 1988.*
Stratagene Catalog (1994), p. 93. Published by Stratagene Cloning Systems, 11011 North Torrey Pines Road, La Jolla, California 92037.*
Cardullo et al., Detection of nucleoc acid hybridization by nonradiative fluorescence resonance energy transfer. Proc. Natl. Acad. Sci. USA 85, 8790–9794, 1988.*
Xu et al., Chemical Chemistry, vol. 38, No. 10, 1992, "Simultaneous Quadruple–Label Fluorometric immunoassay of Thyroid–Stimulating Hormone, 17α–Hydroxyprogesterone . . .".
International Publication No. WO 91/00511, published Jan. 10, 1991.
International Publication No. WO 96/13612, published May 9, 1996.

* cited by examiner

Primary Examiner—Ethan C. Whisenant
Assistant Examiner—Frank Lu
(74) Attorney, Agent, or Firm—Arent Fox Kintner Plotkin & Kahn

(57) ABSTRACT

The combination of two mechanisms of detection in a single device yields a method which allows the simple quantification of analyte determinations. Suitable formats and reagent kits are suggested.

Figure 1:
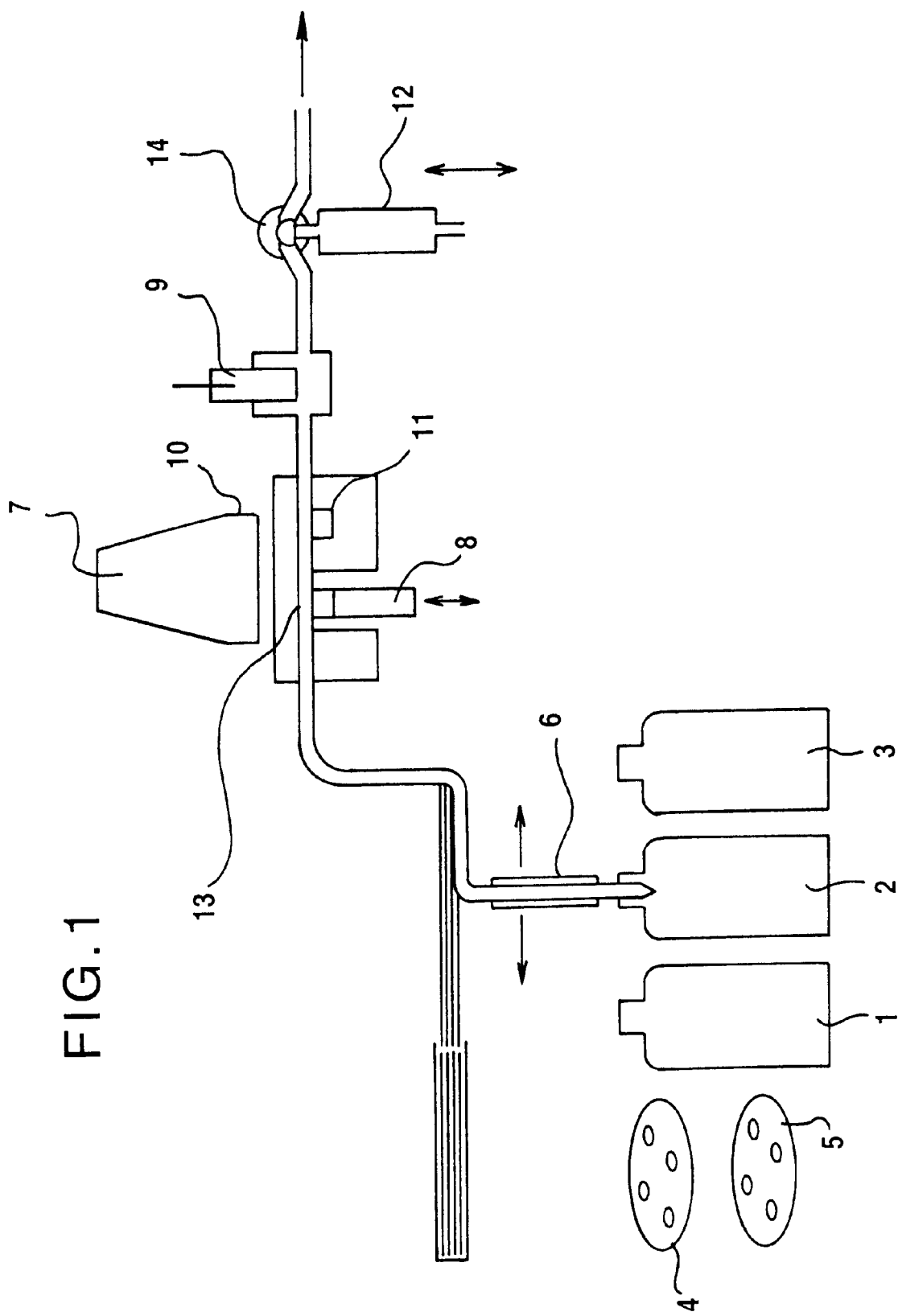

32 Claims, 6 Drawing Sheets

SEQUENCE LISTING (1) GENERAL INFORMATION:

(iii) NUMBER OF SEQUENCES: 7

(2) INFORMATION FOR SEQ ID NO: 1:

(i) SEQUENCE CHARACTERISTICS:
       (A) LENGTH: 21 base pairs
       (B) TYPE: nucleic acid
       (C) STRANDEDNESS: single
       (D) TOPOLOGY: linear (ii) MOLECULE TYPE: other nucleic acid
       (A) DESCRIPTION:  /desc = "Oligodesoxyribonucleotide"

(iii) HYPOTHETICAL: NO (ix) FEATURE:
       (A) NAME/KEY: misc_feature
       (B) LOCATION:1
       (D) OTHER INFORMATION:/note= "A at the 5' terminus
           labelled with Bio-Link I with biotin"

(ix) FEATURE:
       (A) NAME/KEY: misc_feature
       (B) LOCATION:21
       (D) OTHER INFORMATION:/note= "A at 3' terminus labelled
           with AM III with BPRu"

(xi) SEQUENCE DESCRIPTION: SEQ ID NO: 1:

AGACCACCAA ATGCCCCTAT A                                              21

(2) INFORMATION FOR SEQ ID NO: 2:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: other nucleic acid (A) DESCRIPTION:   /desc = "Oligodesoxyribonucleotide"

(xi) SEQUENCE DESCRIPTION: SEQ ID NO: 2:

CAGAGTTCTA TAGTGCTATG                                                    20

(2) INFORMATION FOR SEQ ID NO: 3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "Oligodesoxyribonucleotide"

(xi) SEQUENCE DESCRIPTION: SEQ ID NO: 3:

CATAGCACTA TAGAACTCTG                                                    20

(2) INFORMATION FOR SEQ ID NO: 4:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "Oligodesoxyribonucleotide"

(xi) SEQUENCE DESCRIPTION: SEQ ID NO: 4:

GTCTCTCATC GAGACAAAGT G                                                  21

(2) INFORMATION FOR SEQ ID NO: 5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "Oligodesoxyribonucleotide"

(xi) SEQUENCE DESCRIPTION: SEQ ID NO: 5:

CAGAGTTCTA TAGTGCTATG                                                    20

(2) INFORMATION FOR SEQ ID NO: 6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "Oligonucleotide"

(xi) SEQUENCE DESCRIPTION: SEQ ID NO: 6:

CAGAGTTCTA TAGTGCTATG                                                    20

(2) INFORMATION FOR SEQ ID NO: 7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear -continued (ii) MOLECULE TYPE: other nucleic acid
    (A) DESCRIPTION: /desc = "Oligodesoxyribonucleotide"

(xi) SEQUENCE DESCRIPTION: SEQ ID NO: 7:

CATAGCACTA TAGAACTCTG                                                         20

DETERMINATION OF ANALYTES BY MEANS OF TWO MARKERS

Subject matter of the invention is a method for the determination of an analyte in a sample, a reagent kit for performing this method and the use of two differently labeled probes for the quantitative determination of an analyte in a sample.

The determination of an analyte in a sample has acquired especial importance particularly in the field of health care. Many analytes e.g in body fluids can be used to provide an indication for the presence of an illness or an infection. Many analytes are however not directly determinable or are present in small quantities alongside a large amount of a very similar substances contained in the sample such that direct detection is practically impossible. For this reason increasingly the specific determination of an analyte is attempted with the aid of detectable, labeled probes. Ideally these probes bind only to the analytes and thus labeling the analyte. In the meantime a plurality of labeled groups are available. These include for example metals, chromophores, fluorescent markers but also enzymes, electroluminescent groups and chemically activatable groups.

In WO 92/14139 for example a device is described for performing a binding test for an analyte to be determined which is based on electrochemiluminescence. In this case an analyte is determined by virtue of its binding to a labeled probe using metal complexes and excitation of the complex by applying an electrical potential. The light signal generated is then detected.

Similarly calcium-activatable photoproteins have been suggested as labels e.g. in EP 764 468. The mechanism of light generation in these proteins is based on the addition of a calcium-salt-containing solution to a solution containing an analyte labeled with a probe which has been labeled with aequorin. This triggers the generation of an electromagnetic signal by aequorin.

Nucleic acids are particularly useful aids in the field of diagnostics because of the information stored in their base sequences. Special nucleic acid sequences however are present in a much lower quantity than very similar sequences. It has therefore proven to be of advantage to amplify the nucleic acids to be detected prior to their detection, i.e. production of a plurality of copies of a certain sequence. The Polymerase Chain Reaction (PCR) (U.S. Pat. No. 4,683,202) is such a method. Particularly in this amplification reaction it has been discovered that a quantitative detection of nucleic acids is not possible or is only possible under very favorable conditions because the amplification efficiency is heavily influenced by different factors. Therefore it has been suggested that a standard analyte be added in a known amount to the analyte-containing sample prior to amplification. The standard should differ from the analyte in its detection properties but behave in a similar manner with respect to its amplification efficiency. Such a polymerase chain reaction which makes use of internal standards is for example described in U.S. Pat. No. 5,213,961 or U.S. Pat. No. 5,219,727. Similar methods are described in WO 92/01812, WO 94/04706, EP-A-0 525 882, WO 95/02067 and WO 94/09156. In the last-named patent application a method is described in which an immobilized primer is used in the PCR and the amount of amplification achieved is determined using probes.

In WO 93/10257 a method is described in which firstly PCR is performed and then the reaction mixture incubated with two differently labeled probes.

In WO 89/10552 an apparatus for the simultaneous determination of two samples using different labels which can be excited to electrochemiluminesce is described. Two measuring cells and two detectors are used which generate different wavelengths which are then detected. Method in which the excitation step functions in a manner which is spacially and chronologically separate to guarantee acceptable dynamics and sensitivity have the disadvantage that the sample throughput is small and the amount of sample volume required is large.

DE-C-3022426 describes an immunoassay in which a chemiluminescent label is excited to the point of emission by oxidation products produced by the application of an electrical potential.

In EP-0 478 626 a detection group is described which is modified by various substances in such a manner that the resulting detection group displays different kinetic behavior or exhibits a different spectrum. Excitation occurs simultaneously using the same trigger (oxidative). The signals (spectral or kinetic) in practice overlap to a very large extent such that reduced dynamics and lowered sensitivity result.

In EP-0-199 804, U.S. Pat. No. 5,238,808 and U.S. 5,310,687 a multi-labeling system is described in which the various labels are detected optically making use of their differing spectral characteristic.

In WO 93/01308 a method for detecting an analyte using acridinium ester-labeled antibodies and generation of a chemiluminescent signal by oxidation at an alkaline pH is described.

One object of the present invention was therefore in part or in whole to improve on the state of the art and in particular to make available a method in which the disadvantages of previous simultaneous fluorescence excitation methods (non-resolvable or poorly resolved signals) are avoided and at the same time increasing the throughput of the analyzer.

Subject matter of the invention is therefore a method for the determination of an analyte in a sample by incubation of the sample with at least two probes of which at least one is specific for the analyte to be determined and whereby the at least two probes carry different labeling groups, each being capable of generating a different electromagnetic signal for each different labeling group and evaluation of the signal generated is taken as an in indication of the presence of an amount of the analyte. Another subject matter of the invention is a reagent kit for the determination of an analyte and the application of two probes which can supply two different electromagnetic signals for the quantitative detection of analyte in a sample.

In FIG. 1 the schematic construction of a device is shown for the performance of the method according to this invention.

Figure 2:
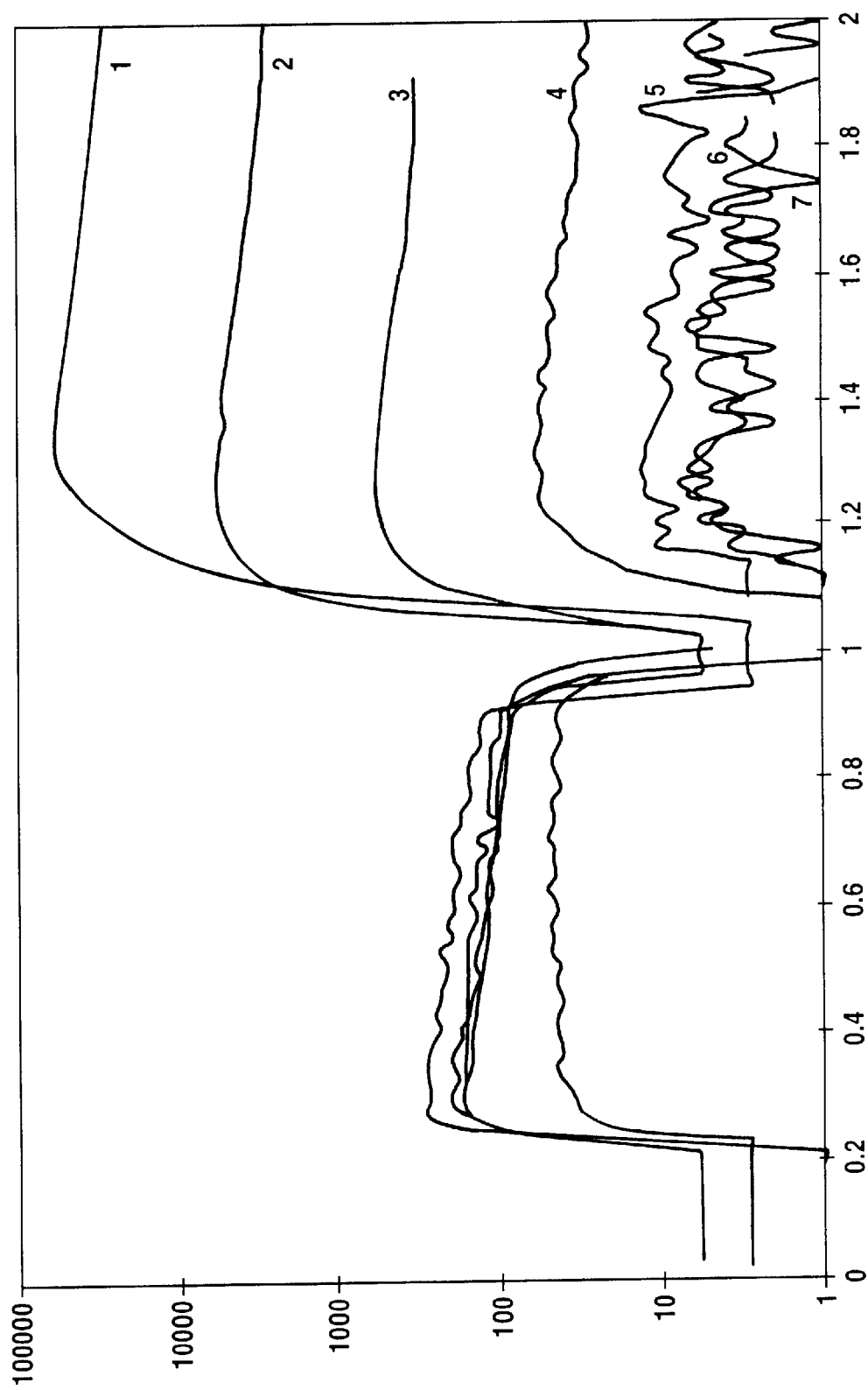

In FIG. 2 the progression of the signal for the determination according to this invention at different analyte concentration is shown.

Figure 3:
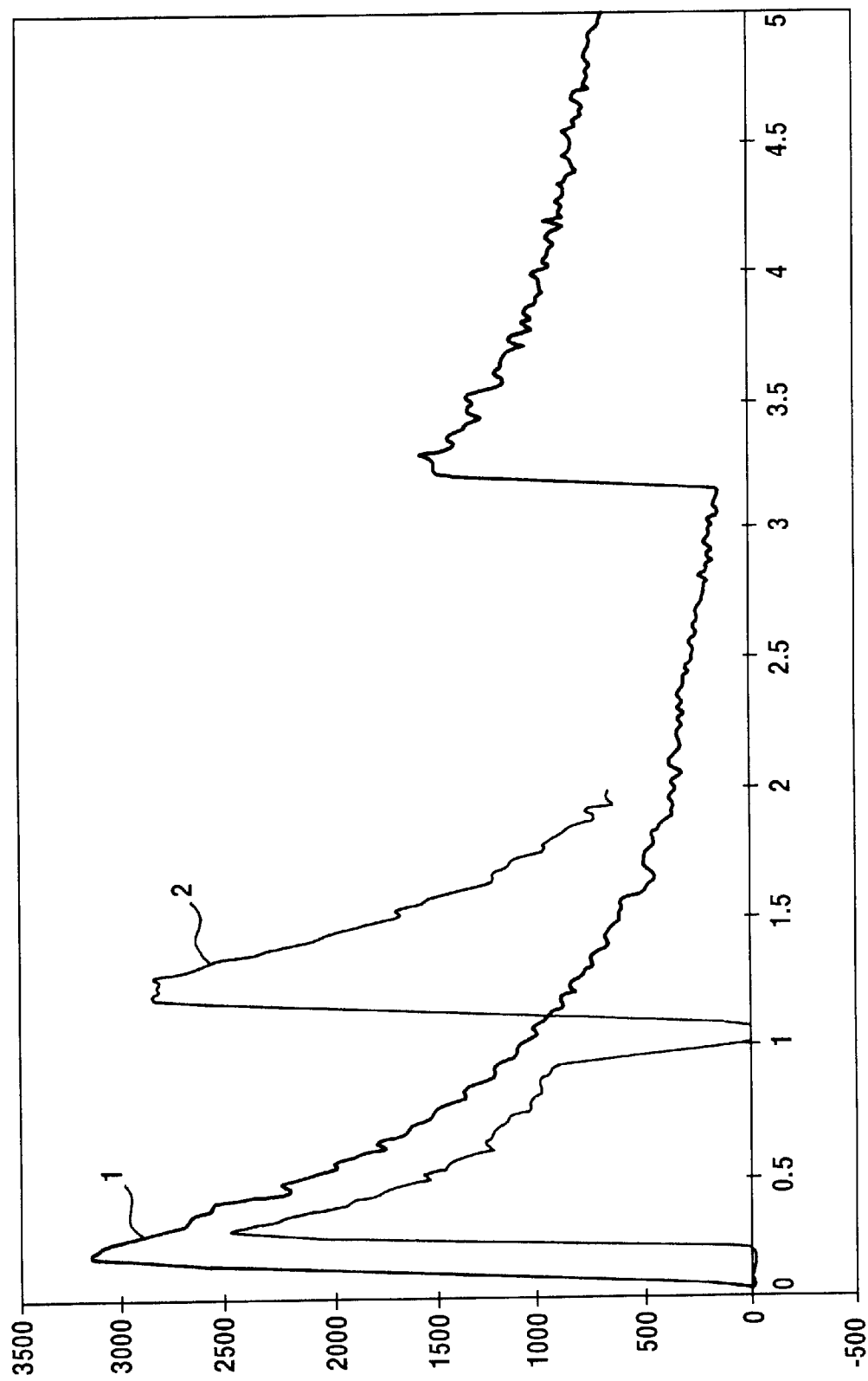

In FIG. 3 a comparison between two exemplary methods according to this invention is made in which the detection reactions have been lateraly separated.

Figure 4:
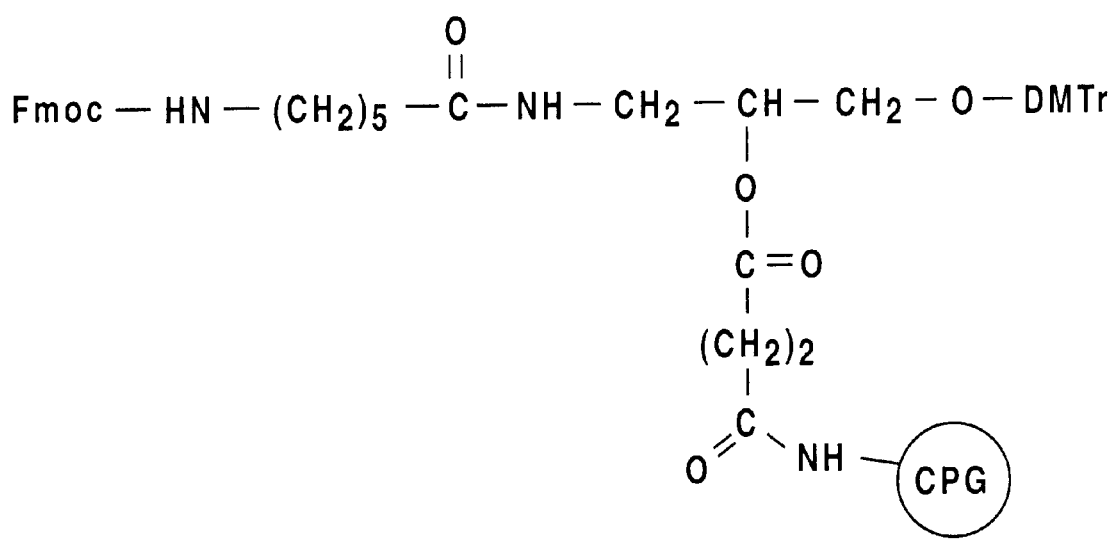

In FIG. 4 a structure of a linker molecule for the linking of a label is shown.

Figure 5:
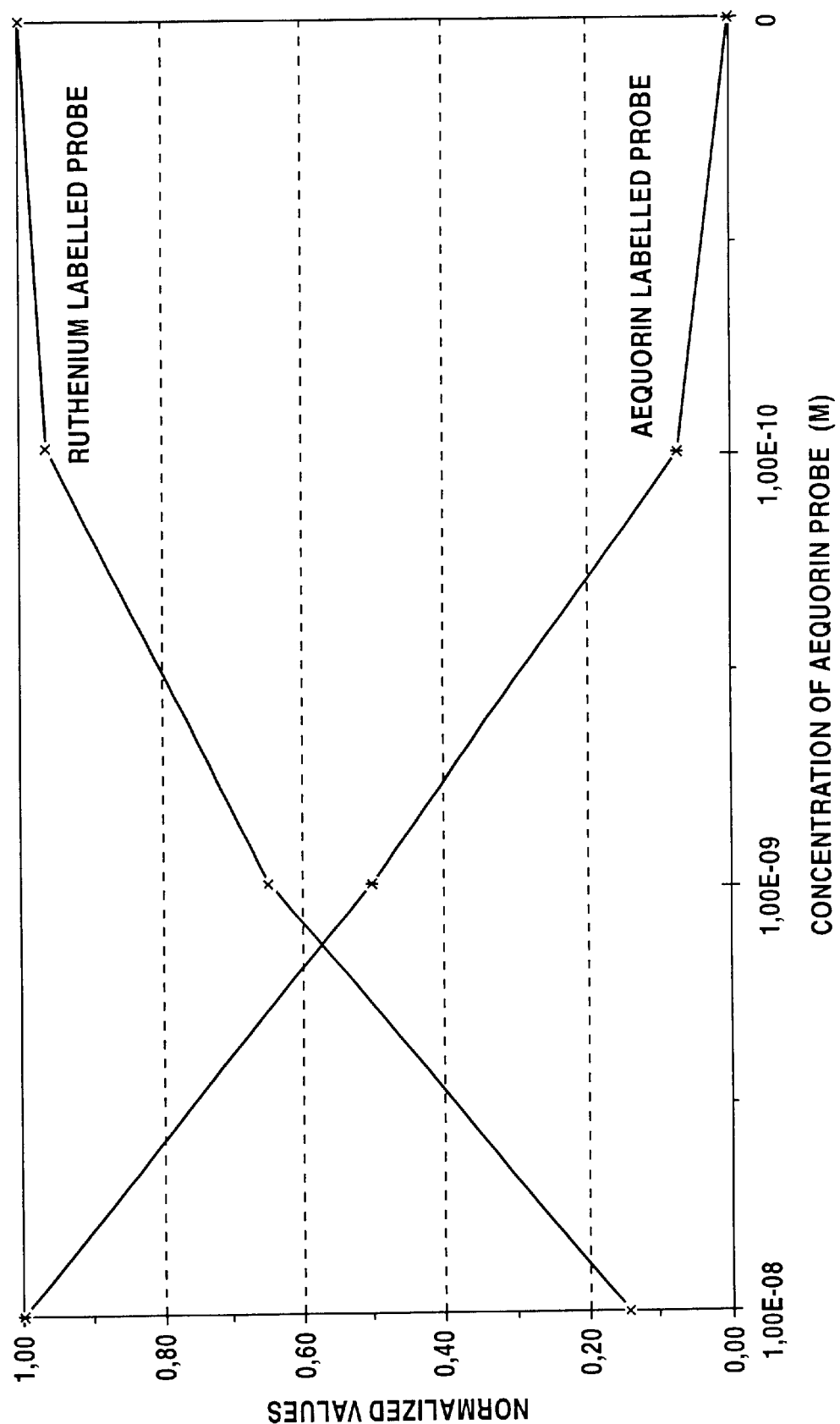
Figure 6:
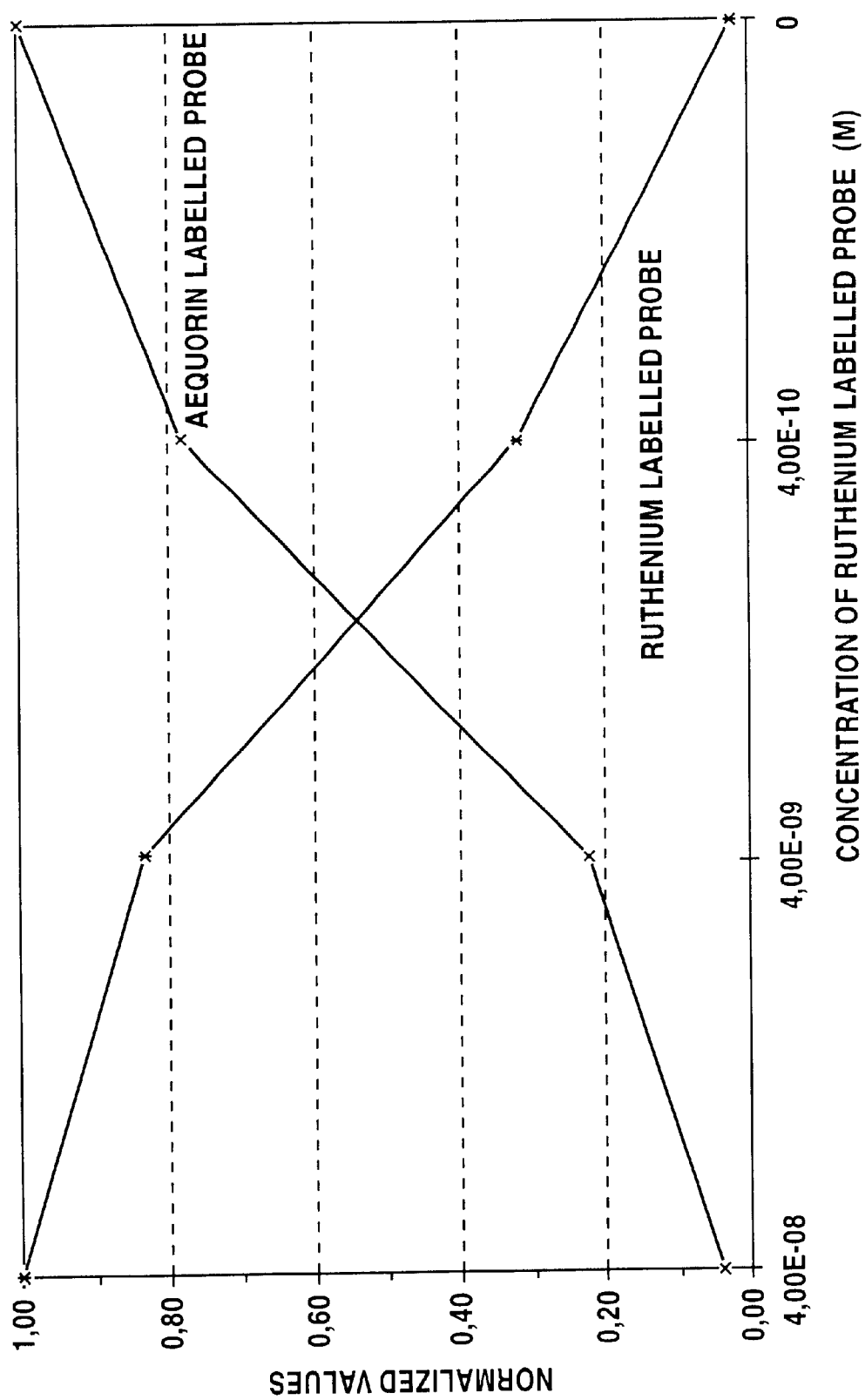

In FIGS. 5 and 6, the result of a competitive test between two differently labeled probes competing for the same target is shown.

Analytes according to this invention are all materials which are the subject matter of the method of determination. These are preferably components of samples which are used in medical diagnostics, i.e. in particular ingredients of body fluids such as antigens, antibodies, cells or nucleic acids. The nucleic acids can be nucleic acids which are specific to an infective agent e.g. viruses or materials of bacterial origin, i.e. viral or bacterial nucleic acids or organism-endogenic nucleic acids. One determines whether the amount is different to the amount found in the normal state e.g. mutations, deletions or insertions in one or more positions. Viral nucleic acids are for example ribonucleic acids of RNA viruses e.g. HCV, HIV or HGV or genomic DNA or rRNA of bacteria, e.g. chlamydia, neisserien or salmonella.

According to this invention a sample is a liquid sample in particular in which the analyte to be determined is dissolved or suspended. A sample of a body fluid is preferred, e.g. blood, urine or sputum or fluid derived from these such as serum, plasma, buffy coat or a liquid which is produced after execution of one or more reaction steps. These reaction steps take place preferably after addition of reagents and can effect an enrichment, modification or replication of the analyte in the original sample material or effect the degradation of interfering substances in the original sample. Especially preferred sample materials are reaction mixtures which are produced after execution of sample preparation and subsequent execution of PCR. A probe, as understood in this invention, is a component of a detection system for an analyte to be determined or/and a standard analyte. Such components are for example those which detect the analyte or the standard analyte by virtue of biological interactions, e.g. immunological interactions or base pairing interactions between a complementary sequence of base pairs of nucleic bases sufficient in number for hybridization to occur. Probes are preferably therefore an antibody, an antigen, a hapten or a nucleic acid or a nucleic acid analogue which for example differs from natural nucleic acids in that the saccharide phosphate backbone is substituted for by a peptide backbone (e.g. as in WO 92/20702).

The method of the invention uses at least two probes of which at least one is specific for the analyte to be determined. A probe is defined as being specific when under the test conditions it exhibits a cross-reactivity of less than 5% with other e.g. not-to-be determined sample components or components expected to be present in the sample, i.e. such other components bind less than 5% compared to the bound quantity of the desired components i.e. the analyte.

Preferred is the use also of at least one further probe which is not specific for the analyte to be determined. The probe is preferably specific for a further ingredient of the sample, in particular a component which differs in a small but defined way in structure from the analyte. A standard analyte is preferably the additional component of the sample.

According to this invention a standard analyte is a material which is contained in the sample in a certain defined amount, preferably a known amount or is added to the sample in a known, defined amount. The standard analyte differs in a defined way from the analyte, e.g. in its capacity to bind to the analyte-specific probe, which under the preferred test conditions does not bind to a significant extent. The standard analyte can already be present in the original sample but is preferably added to the sample prior to incubation of the sample with probe. In the event of the determination of a specific nucleic acid in a sample, the standard analyte is preferably also a nucleic acid which differs from the analyte nucleic acid either in its nucleotide sequence or in the length of the chain. In particular, a partial segment of a nucleic acid having an analyte base sequence is preferably removed and a segment of another (preferably a sequence not contained in the analyte) inserted using recombinant technology to prepare a standard nucleic acid. In this case, the analyte nucleic acid structure does not have to differ from the standard analyte nucleic acid with respect to its chain length to a significant extent from the standard nucleic acid. Not only a segment of the analyte nucleic acid but also a segment of the nucleic acids is preferably subjected to an amplification procedure and preferably a procedure for the multiplication of the said sequences, e.g. with the aid of a polymerase chain reaction as described in U.S. Pat. No. 4,683,202. To effect this, primers are preferably employed which can be used for the amplification of the analyte nucleic acid structure and the standard nucleic acid structure. Generally this method is described as a competitive PCR method and is described for example in U.S. Pat. No. 5,213,961.

In the case described above using a standard nucleic acid, the nucleotide sequence of the first probe (analyte probe) is selected in such a manner that it can hybridize with a region of the analyte or the amplification product of an analyte partial sequence which is not present in the standard nucleic acid whereas the second probe (standard probe) has a sequence which has been selected such that the primer elongation product can only hybridize when the elongation product has been formed by primer elongation using the standard nucleic acid as a template. The probes are preferably oligonucleotides or peptide nucleic acids (PNA, WO 92/20702). If the first probe is analyte-specific and does not significantly bind the standard analyte, the second probe can be selected such that it is specific for the standard analyte or that it can bind not only the standard analyte but also the primary analyte. The first case outlined is preferred by far.

In the method of invention it is possible in principle to employ two or more probes which are specific for a corresponding number of different analytes to be determined. In this case the advantages of the invention are apparent.

An essential significant feature of the invention is the fact that at least two of the probes carry different labeling groups. In the most simple case, two probes are employed of which each carries a different labeling group. Of these two probes, one is specific for the analyte to be determined. In further embodiments of the invention one or more of these probes can carry several labeling groups, e.g. one probe having two labeling groups. This can lead to an increase in the sensitivity. It is however also possible to use more than two probes to determine several analytes which would carry more than two different labeling groups. In this case each probe can contain one or more of the same labeling group. The case should be avoided in which the probe carries two different labeling groups in accord with this invention.

The probes are added to the sample in an amount and concentration which are adequate for sufficient binding of the probe to the one or several analytes or the standard analyte. However because in many cases the amount of analyte present is not known, the probe is usually added in a stoichiometric excess compared to the maximum conceivable amount of analyte. This is especially applicable when quantitative evaluation of the method is intended.

In accordance with the invention it is not necessary to split the sample after amplification and to add the probes to each aliquot. The probes are preferably incubated together with the sample and not separately. Relatively small amounts of sample are then required.

A labeling group in accordance with this invention is a group with can be bound directly or indirectly to the probes. Moreover, the labeling groups can be subdivided into two types, namely such groups which themselves are not capable of generating a sufficiently large electromagnetic signal for detection and groups which can directly generate an electromagnetic signal. Labeling groups of the latter group are also termed detection groups in the following. Groups which themselves do not generate an adequate electromagnetic signal for the purposes of detection are preferably all groups which are detectable via biological interactions as described above for the interaction of the probe and the analyte, e.g. haptens, digoxigenin according to EP-B-0 324 474, or vitamins, e.g. biotin. Digoxigenin can for example be detected by an antibody against digoxigenin and biotin with the aid of avidin, streptavidin or antibiotin/antibodies.

In the case of indirect labeling, the use of a conjugate in the method of invention from one of the said detectable group recognizing components (antibodies, avidin etc.) and a group capable of generating an electromagnetic signal (detection group) is preferred. This conjugate can be added to the sample incubation mixture with the probes even at the beginning of the incubation period, however the addition of conjugate after completion of the incubation of the probes with the analyte is preferred without separation or after separation of non-analyte bound analyte specific probes from the analyte-bound probes.

Furthermore, it has proven to be highly recommendable after incubation of the sample with probes to separate non-analyte bound analyte-specific probes from the analyte-bound probes as well as further sample component-bound probes from non-bound probes. The same is also valid for the separation of non-bound conjugates. This separation process can advantageously occur when the binding product of the analyte or further components present in the sample or the standard analyte bind with the appropriate probes present on the surface of a solid phase (a solid in the form of a bead) and the remaining liquid phase is separated from the solid phase. This can for example occur by retaining the solid phase in a filter and allowing the liquid to pass through the filter. The use of a magnetic solid phase opens up another possibility and subsequent application of a magnetic field to collect the magnetic solid phase at a certain collection point. The liquid containing the non-bound probes can then be removed. An embodiment of the invention is also preferred in which physically bound probes are removed from the solid phase using washing solution while probes which are specifically bound to the analyte or other components are not removed. The binding of the analyte to the solid phase is however dependent on the type of analyte to be determined. Therefore biological interactions (preferably however of another type or/and specificity to the binding of the analyte or standard analyte) can be used for the purposes of binding. In the event that the analyte is an antigen, then binding to the solid phase can occur, the surface of which has been modified by the binding of an antibody against this antigen to it. In the event that a nucleic acid is the analyte in question, then the binding can occur using probes which have a nucleic acid sequence which is complementary to a sequence to be found in the analyte primary structure, of the further sample components or the standard nucleic acid. A preferred sequence for this capture probe is a sequence which is bound to the solid phase by covalent or via biospecific e.g. biotin/streptavidin bonds or is selected in such a manner that it is not only a complementary sequence to a partial sequence of the analyte but also the standard nucleic acid or other analyte nucleic acid sequences. This is advantageous to the extent that for the capturing of both sample components only one type of capture probe is required. In the event that the analyte is a cell, then these cells can be immobilized by antibodies raised against antigens present on the surface of the cell (e.g. CD3 for T-cells). The selection/detection can occur using antibodies raised against sub-groups (e.g. T-helper cells with CD4 having a first labeling group, of T-suppressor cells with CD8 and a second labeling group).

A further possibility of binding the analyte to the nucleic acid or the standard nucleic acid to a solid phase is by incorporating an immobilized group in the copy generated during the nucleic acid amplification procedure. This can occur by using immobilized labeled primers or immobilized labeled mononucleosidetriphosphates. Biotin can be selected as the immobilized group. The resulting amplification product can be captured using a streptavidin-coated surface.

Based on the presence of labeling or detection groups, an electromagnetic signal is generated for each sort of labeling or detection group which can be assigned to the presence of labeling or detection groups. Suprisingly it has been discovered that the combination of groups which can be excited by differing means for different probes is particularly advantageous. Of advantage is for example the combination of a probe, which can be excited to luminesce using electricity (electrochemiluminescence, ECL) with a probe which can be excited to luminesce by chemical means (bioluminescence). Selective, i.e. targeted generation of a signal by excitation drastically lowers or even avoids cross-reactivity, i.e. concomitant excitation of labeling groups which are not to be detected. This gives rise to a large dynamic range for the whole method and a relatively low background noise (high sensitivity). This type of generation depends upon the individual requirements with respect to signal generation. A first category of labeled groups is characterized by the fact that the signal is generated by bringing the labeling group into contact with certain (e.g. chemical) reagents. A preferred category of detection groups which can be excited to bioluminesce, e.g. allosterically triggerable groups. The detection groups of different probes belong preferably to different substance classes (e.g. small molecular weight organic metal complexes and a protein). Photoproteins which can be activated by ions belong to the category of labeling groups (apo-photoproteins: native or produced by recombinant technological means). Aequorin, obelin, mitrocomin, thalassicolin and clytin are representative of this group of photoproteins. These proteins share the characteristic that they emit light when they are activated so that an amount or the presence of a substance can be determined by measuring the light emitted. The use of such photoproteins is described in the literature by Cormier, M. L. et al., Photochem & Photobiol. 49/4, 509–512 (1989) or Smith, D. F. et al., in Bioluminescence and Chemiluminescence: Current Status (P. Stanley & L. Kricka, eds.), John Wiley and Sons, Chichester, U.K. 1991, 529–532 for conventional tests and the mechanism by which the signal is generated. In this case the activation occurs by addition of calcium ions to the labeled bound probes.

Adequate chemiluminescent direct labeling groups exhibiting a lightning-discharge like profile are for example acridinium arylester, acridinium acyl sulfonamide or isoluminol derivates, such as ABEI, AEEI and AHEI.

Metal complexes which can be excited to electrochemiluminesce represent a particularly suitable category of labeling groups. Such complexes are for example described in EP-A-0 199 804, EP-A-0 265 519, WO 89/04302 and WO 92/14139. Ruthenium complexes which incorporate bipyridyl moieties as ligands are preferred. Nucleic acids which are labeled with special ruthenium complexes are for example described in EP-A-0 340 605. EP-A-0 178 450 describes ruthenium complex labeled immunological probes which can be used very well in the method of invention. In addition to ruthenium complexes, other transition metals (osmium, iridium etc.) which can be triggered to electrochemilumisce or other heterocyclic aromatic complex ligands suitable for the purposes of electrochemiluminescence can be used.

In the method of the invention detection groups which are capable of generating a detectable signal traceable to the group are excited. The signal is preferably a luminescence signal. Normally luminescence is understood to be a process in a which a chemically excited, metastable molecular state relaxes to a lower energy state after emission of a photon (electromagnetic radiation).

Processes leading to an independent generation of a signal are defined in the context of this invention as processes in which a certain labeled group is selectively excited in the absence of excitation of other labeling groups located on other probes. An electromagnetic signal is taken to mean in the context of this invention a light signal. Flash discharges of light are particularly preferred.

Various types of electromagnetic signal will be discussed in the following when the signals stem from different origins e.g. originating from different substance categories of labeling groups. In the following a combination of electrochemiluminesce and bioluminesce using photoproteins is understood to mean a preferred embodiment of a system composed of two luminescent labels which can be excited by different means.

The generation of the various electromagnetic signals can occur simultaneously or consecutively. This is particularly dependent on whether the signals are so different in nature that they can be detected simultaneously. It has however proven to be practical to generate the various electromagnetic signals one after the other and to detect them. Therefore selection of labeling groups which can be selectively activated is preferred, i.e. the first group is activated by chemical or/and allosteric triggering and the second group by electrochemical triggering. A particular advantage is that the reaction conditions required for the generation of the signal do not have to be reproduced in the same solution. In the event that the first labeling group is an ion-activatable photoprotein and the second labeling group is an electrochemically excitable metal complex, it is possible to determine the signals generated simultaneously or consecutively. Simultaneous determination is possible using labeling groups having different emission spectra. The module used for the detection of light has to facilitate spectroscopic resolution of the signals e.g. by suitable selection of the filter, prisms or grating. In case consecutive determinations of signals is employed the conditions necessary for the generation of a photoprotein signal can be sent first but preferably creating the conditions necessary for the generation of an electrochemiluminescent signal are set first. For this purpose (for the example in which labeling occurs using a ruthenium trisbipyridyl complex) a solution of potassium phosphate, tripropylamine and Thesit™ is brought into contact with the analyte bound to the solid phase, the standard analyte and possibly other components which are to be determined, to which the probes are bound. This can take place either by adding the solution to the solid phase by pipetting but is also possible however by adding the solid phase to a solution of the reagents or by allowing a solution of the solid phase to flow by. The latter case is preferred because in this case cleansing is also effected. In the presence of two or more probes, electrochemiluminescence is generated by application of an electrical potential. The light emitted is converted from a signal to a measured value using suitable instrumentation, e.g. using a photomultiplier. Referral should be made to the following publication for measurement conditions and reagents: Uland, J. K. and Powell, M. J. in J. Electrochem. Soc. 137, pp. 3127–3127 (1990). Surprisingly generation of the electrical signal does not interfere with the photoprotein activity.

Thereafter, reaction conditions are created which are required for the generation of a signal based on the presence of a photoprotein. In this case too the appropriate reagents can be added to the solution present or an appropriate wash solution or to the solid phase. The displacement of the reagent solution required for the generation of electrochemiluminescence by the reagent solution for activatable photoproteins is preferred. The contacting of the photoprotein with the activatable ion also generates a light signal whose intensity can be measured by the instrumentation and converted to a measured value. It was also possible to determine the signal generated with the aid of aequorin using the same arrangement of apparatus used for the detection of light generated with the aid of the rutheniumbipyridyl complex providing that the photomultiplier was sensitive to both wavelengths. Referral to the publication by Smith, D. F. et alt Bioluminescence and Chemiluminescence; Current status (P. Stanley and L. Kricka, eds.), John Wiley, Chichester, U. K., pp. 529–532 (1991) has been made in this case for the conditions required for the generation of a light signal using aequorin.

Flash discharge signals are preferred and are of advantage. This means that the excitation leading to the signal and the measurement of the signal occur very rapidly. The total time required for both detection reactions to occur is not significantly longer ($\geq 2.5$ x) than for both single determinations (e.g. electrochemiluminescence: 4 seconds, electrochemiluminescensce with subsequent bioluminescence using aequorin: 5 seconds). This facilitates maximum throughput (especially on analyzers) because the principle of dual labeling detection is not compromised when the measuring window is broadened. For the combination described, there is no interference between both signal reactions assigned to one probe and chronological resolution occurs within a measuring window so that a clean, respectively independent direct evaluation of both signals is possible without the need for the application of a mathematical correction algorithm to supply an approximate value in the final instance. The respective performance of both labeling groups (e.g. concerning criteria such as analytical sensitivity, series and day-to-day precision, dynamic measuring range and linear measuring range) remains unaltered to advantage in the combination described.

The determination of signals generated by different detection groups occurs preferably using the same analytical arrangement e.g. in the same measuring cell. Preferably the measuring cell is selected such that the measuring cell does not have to be altered to detect the wavelengths emitted by both. The measuring cell is preferably constructed to accommodate the electrochemical trigger for a detection group. The subsequently occurring detection step is based on another substance category of detection groups and does not employ the electro-arrangement of the ECL measuring cell for the excitation process to produce luminescence but rather just detection.

The sequence of steps which must be executed to detect different detection groups disposes of the necessity of the groups exhibiting different kinetic characteristics or having different spectral behavior. The ruthenium complex can therefore be substituted by a fluorophor which emits light in the blue-green range like aequorin.

The evaluation of the signal or the measured value for these signals depends on the nature of results required from the method of determination. In any case the presence of a measured value which differs from the measured value obtained from a calibration method in which a probe or an analyte was not present is indicative of the presence of an analyte. The same is also valid for measured values of all other components or a standard analyte. This can be used to obtain a qualitative indication of the presence of the primary analyte or other analytes. The result of the determination of the standard analyte can be used in a qualitative determination for the calibration of the system and as a positive control. A preferred embodiment of the method of the invention comprises the following steps:

binding of the analyte and possibly a further analyte or a standard analyte to the solid phase (e.g. a magnetic particle), binding of the probe to an analyte or an additional analyte or the standard analyte, determination of the bound first probe (in the presence of, however independent of, the second probe), determination of the binding of the second probe (in the presence of and independently of the first probe ), determination of the presence or concentration of the at least one analyte by evaluation of the signal generated by the first probe. In this respect further probes labeled with other labeling groups and making use of an independent means of excitation. The analyte, additional analyte or standard analyte and the probes bound there are preferably removed from the site of excitation or measurement after performance of the determination to be then available for further determination e.g. determination of an analyte from another sample.

The method of the invention is however especially suitable for the quantitative determination of the analyte. A quantitative determination in this context is defined as the determination of an amount of an analyte in a primary sample used for the production of the primary sample. In the quantitative determination use of at least one probe is preferred which is specific to the analyte to be determined. If several analytes are to be determined, further probes/labeling groups are required. Moreover a probe is used which is specific for the standard analyte. Because the amount of standard analyte is defined and known, the measured value obtained from the standard analyte can be used to calibrate the measured value for the analyte.

The calibration of the system can be performed for example in the following manner:

I. Constructing a calibration curve:

Different solutions, e.g. 5, with different but known concentrations of analyte-nucleic acid are enriched with the same known amount of standard nucleic acid (e.g. 1000 copies). To each of these solutions solutions having at least two probes are added (e.g. ruthenium labeling of the analyte probe, aequorin labeling of the standard probe). After hybridization the measured signal for the known concentration of analyte and the standard is obtained. A calibration curve is plotted using these values in which the signal relationship from the determination of the analyte compared to the standard is plotted depending on the known analyte concentration used.

II. Sample measurement and evaluation

Prior to the measurement, the same concentration of standard nucleic acid used for the construction of the calibration curve (i.e. 1000 copies) is added to the sample containing the unknown concentration of analyte. The relationship of the signal from the analyte to the signal from the standard is calculated and the analyte concentration read off the calibration curve.

Comparing the relationship between 2 or more signals generated together (i.e. from a reaction mixture) provides a simple possibility to compensate for the fluctuations in signal generation. Possible fluctuations in the amplification reactions of the different probes for the analytes or standards can thus be compensated for. Such fluctuations cause for example variable efficiency factors from sample to sample or for the same sample from cycle to cycle and originate from fluctuations in the quality of the sample preparation (e.g. degree of purification, separation of inhibitors) by making use of an internal, co-amplified standard and ratiometric evaluation are compensated for by computation in each reaction batch. If the signal relationship between the individual analyzers and over the time per analyzer remain relatively constant, this signal relationship can be predetermined by the manufacturer of the instrument or the reagent for the purposes of evaluation can be implemented in the software routine using a correction factor or a correction function. The customer then only has to create a calibration curve using values from different concentrations of analyte nucleic acid.

III. Prior to the construction of the calibration curve, an experimental check is made on the comparability of the amplification efficiency (yield) of sample DNA and standard DNA(internal standard), recognizable from for example the parallel linear progression of the plot of log signal (Y) against log initial number of copies $N_0$ (X).

In FIG. 1 the diagrammatic construction of an instrument on which the method of the invention can be performed is shown. An appropriate instrument which can be easily adapted such that the method of the invention can be performed on it can be obtained from Boehringer Mannheim GmbH (Elecsys 2010 or 1010).

The following steps are preferably performed:

1. Amplification (using PCR) of an analyte nucleic acid present in the sample and co-amplification of a known amount of a standard nucleic acid.
2. Denaturation by addition of NaOH-solution.
3. Storage of the sample in the sample rotor, 5.
4. Transfer of an aliquot to a vessel in the incubator.
5. Addition of an analyte specific and a standard analyte specific probe.
6. Incubation with streptavidin-coated magnetic particles in incubator 4.
7. Uptake of a sample of solution from incubator 4 using the pipetting needle 6 in the measuring cell 13.
8. Uptake of the conditioning solution from container 1 for transport of the aliquot through the liquid flow system. The magnetic particles with analyte, standard analyte and probes bound to them are retained at the working electrode by magnets.
9. Uptake of conditioning solution from container 1 for washing the beads on the working electrode.
10. Application of an electrical potential between the working electrode and the twin electrode, 10 and 11 respectively (controlled via reference electrode 9) results in the discharge of a light flash. Measurement of the light discharged is performed by the photomultiplier 7.
11. Uptake of the calcium-containing trigger solution from vessel 3 in the measuring cell 13 and simultaneous measurement of the resulting luminescence. The particles are retained in the measuring cell 13 by the magnet 8.

12. Removal of the magnet 8 and therefore transfer of the bound magnetic particles out of the vessel 2 using the cleaning solution which has been pumped through.
13. Evaluation of the signal intensity.
14. The instrument is ready for the uptake of new sample for measurement (step 1)

The subject matter of the present invention can be used to advantage in many ways. Firstly, the method is useful for the performance of quantitative determinations of analytes. The amount of sample liquid required is reduced and possibly even by 50%. When the preferred detection labels are used only one single instrument is required for detection and evaluation. Furthermore, it is also possible to combine immunological tests with nucleic acid-based tests.

The throughput of samples on analyzers is considerably improved in all cases. Using the technique of independent excitation, it is possible to chronologically split the samples. This gives rise to a larger dynamic range and increased sensitivity.

In FIG. 2 an example of signal progression is displayed in the case where two detection groups are determined consecutively (ruthenium complex and aequorin). Clearly the signal intensities are of the same order of magnitude, i.e. suprisingly sufficient signal yield using the aequorin label can be obtained when instruments expressly concipated for the determination of elechemiluminescence are used. In FIG. 2 curves 1 to 7 are as follows:

| | |
|---|---|
| 1 | 10 nM bio-Aeq/7 pM ruthenylated oligonucleotide |
| 2 | 1 nM bio-Aeq/7 pM ruthenylated oligonucleotide |
| 3 | 100 pM bio-Aeq/7 pM ruthenylated oligonucleotide |
| 4 | 10 pM bio-Aeq/7 pM ruthenylated oligonucleotide |
| 5 | 1 pM bio-Aeq/7 pM ruthenylated oligonucleotide |
| 6 | 0 M bio-Aeq/7 pM ruthenylated oligonucleotide |
| 7 | 0 M bio-Aequorin/0 M ruthenylated oligonucleotide |

The intensity versus time in seconds is plotted.

FIG. 3 shows that, surprisingly, practically no signal loss is incurred by first performing the ECL measurement. In FIG. 3 the progression of signal intensity is shown (constant concentration relationship) while the measurement time is shown in seconds for a first case in which the MDP aequorin label (mono-biotin-mono-digoxigenine hepta-peptide, available in Enzymun-Test® DNA Detection, Boehringer Mannheim GmbH, Germany, Cat. No. 1447777) and finally the ECL signal from the oligonucleotide 1 (SEQ.ID.NO. 1) is determined (curve 1) and a second case in which first of all the ECL signal and finally the aequorin signal is measured (curve 2). It is evident that the intensity of the aequorin signal prior to the ECLdetermination differs only to a negligible extent from the intensity of the signal after the ECL-measurement. This means that surprisingly bioluminescensce labels are not perturbed in their function by the electrochemiluminece process which occurs at first. The trigger threshold potential for the ECL determination is beyond the dissociation potential for water i.e. water oxidation occurs during the electrochemiluminescence process at the anode (where aequorin is located) and therefore large amounts of oxygen are generated. The protein environment is hence substantially perturbed. Surprisingly the magnitude of the signal produced by the protein is not affected. One must however still guarantee that the remainder of the reaction solution left over from the previous determination does not remain in the measuring cell in an amount which would interfere. This is especially valid for substances (e.g. ions), which, when both solutions for the differing reaction meet, form poorly soluble precipitates (e.g. calcium ions from the aequorin triggering process and phosphate ions from the ECL-triggering process). Particularly, the use of completely separate and independently excitable labels in consecutive determination reactions especially for analyzers in which a plurality of determinations should be performed and whereby determinations performed later should be performed in a manner which is just as reliable as the first is not obvious to one skilled in the art. This is especially true for analyzers having flow-through cells which can be used for various determinations.

The subject matter of the invention is also a reagent kit for the determination of an analyte in which two or more probes are contained in one or separate containers of which at least one is specific for the analyte to be determined whereby the at least two probes carry different labeling groups capable of generating different electromagnetic signals. The specificity of the other probes can be extracted from the above description of the method of the invention. Moreover, the reagent kit preferably contains a container with a standard analyte whereby the concentration of the standard analyte is known or/and is predefined. Furthermore, the reagent kit can contain other reagents which are necessary for the determination of the labeling groups. The reagent kit may also contain reagents suitable for pretreating samples to produce a solution containing analyte and which is suitable for performing determinations on. These are preferably contained in separate containers. Suitable reagents are for example primer, enzyme- and mononucleoside triphosphates for the performance of a competitive PCR. Other possible components of the reagent kit are suspensions of magnetic particles to which analytes have been bound. A further subject matter of the invention is the use of two probes which can generate different electromagnetic signals for the quantitative detection of analytes in a sample.

The following examples exemplify the object of the invention:

EXAMPLE 1

Consecutive Determination of Different Detection Groups on Streptavidin-Coated Magnetic Particles in the Presence of Ruthenium Complexes Acting as teh Second Detectable Group A 200 µl buffer solution was prepared for the determination of the different detectable groups containing biotinylated aequorin (in the concentration range 1 pM to 10 nm) and biotinylated with Bio-Link I at the 5'-end (Applied Biosystems Inc., Biotin Amidite, Cat.-No. 401395) and via AM III at the 3'-end (insertion during oligonucleotide synthesis into CPG (Controlled Pore Glass) and removal of the protecting group Fmoc, FIG. 4) using BPRu (prepared according to Clin. Chem. 37/9, 1534–1539 (1991)) labeled oligonucleotide I (SEQ.ID.NO. 1). 36 µg of streptavidin beads were added to the sample solution (Boehringer Mannheim GmbH, Elecsys® TSH Immunoassay, Cat. No. 1731459) in 50 µl of the above-named buffer and incubated for 5 min. at 37 ° C. Thereafter 120 µl of this reaction solution were taken up in the Elecsys 2010-or Elecsys 1010-analyzers measuring cell (Boehringer Mannheim GmbH). Then 1100 µl of a conditioning solution composed of 300 mM potassium phosphate. 180 mM tripropylamine (TPA) and 1.7 mM Thesit® are pumped through. An electrochemiluminescent (ECL) signal was then generated (potential: 1.25 V, time: 0.8 sec.). The ECL-signal was recorded and can be seen on the left hand-side of FIG. 2. The constant concentration of the ruthenium labels ensures that an approximately identical signal is obtained for all ECL-measurements.

For the determination of the aequorin signals a trigger solution composed of 10 mM Tris/HCI, pH 7.4 and 100 mM calcium chloride is forced into the measuring cell. The signal measured is shown on the right-hand branch of the curve shown in FIG. 2. Clearly the signal from the aequorin determination is dependent on the concentration of the aequorin-labeled complex.

EXAMPLE 2

Determination of Two Different Chlamydia-Target Sequences

The following exemplifies a practical situation involving a Duel Label Assay using an internal standard in which an internal standard nucleic acid of known concentration has to be determined in the presence of an analyte nucleic acid of unknown concentration. The potential concentration range of the analyte nucleic acid extends over several orders of magnitude.

For constant quality of quantification over the entire concentration range the standard signal must remain constant and independent of the concentration of the sample. The analyte signal must remain linear as the sample concentration is varied, independent of the concentration of standard nucleic acid which is also present.

In the present example independency of both signals is achieved by making use of binding reactions between two different capture probes performed in parallel (standard or analyte) and two indicator probes each capable of hybridization (standard- or analyte specific) of which one is labeled with Rubpy and the other aequorin. The real test situation is modeled by holding the concentration of one capture probe constant (this simulates the standard), whereas the concentration of the other capture probe (which simulates the standard) varies over four orders of magnitude.

The capture probes are biotinylated 40 mers (20 mere-(or 19 mer-) (not- chlamydia-specific) spacer sequences +20-mer-(or 21-mer-) hybridization sequence). Both hybridization sequences originate from Chlamydia trachomatis genome. In the first instance the hybridization zone has the following sequence 5'-CA GAG TTC TAT AGT GCT ATG-3' (SEQ.ID.NO. 2). The relevant indicator probe (5' CAT AGC ACT ATA GAA CTC TG-3'(SIQ.ID.NO. 3)) is aequorin-labeled (MH:SH linking chemistry after functionalization using basic, activated [N-trifluoroacetamido]-amninoalkyl-phosphoramidite).

The hybridization sequence in the other capture probe is 5'-G TCT CTC ATC GAG ACA AAG TG-3' (SEQ.ID.NO. 4). The indicator probe (5' CA GAG TTC TAT AGT GCT ATG-3' (SEQ.ID.NO. 5)) is coupled to Ru(biPY)$_3$ using NHS.

The concentration of one of the two chlamydia-targets (capture probes) is held constant at 0.1 nM, whereas the concentration of the other is serially diluted as follows $1*10^{-9}$, $1*10^{-10}$, $1*10^{-11}$, $1*10^{-12}$ M. The concentration of both indicator probes is held constant at (10 nM). The hybrids formed at 37° C. are immobilized on streptavidin-coated ECL-beads (720 μg/ml from Elecsys® TSH) and then determined using a Dual Label Cycle as described in example 1.

EXAMPLE 3

Competitive Assay

In this experiment a competitive test is performed using duel labeled detection as a model PCR (qPCR) assay employing co-amplification of an internal standard, whereby a label is unequivocally assigned to the polynucletide to be amplified. The indicator probes represent the variable amount of PCR product which competes to bind with the primer using analyte DNA(hybridization rate as a function of each original number of copies).

a. Experimental Design

A biotinylated 30-mer capture probe (10 dT-spacer sequence+20-mer hybridization zone: 5'-CA GAG TTC TAT AGT GCT ATG-3'(SEQ.ID.NO. 6)) is serially diluted down to 1000, 100, 10 pmol/l (also 0 pmol/l=buffer blank) and each immobilized on streptavidin (SA)-coated ECL-beads (720 μg/ml). A base-sequence complementary 20-mer indicator probe (5'-CAT AGC ACT ATA GAA CTC TG-3' (SEQ.ID.NO. 7)), coupled to a functional group with basic (NH$_3$) activatable [N-trifluoracetamido]-aminoalkyl-phosphoramidite on the one hand using MH:SH-linking chemistry labeled with aequorin, and on the other hand via NHS-chemistry using Ru$^{2+}$ (bipy)$_3$ is allowed to react with the capture probe whereby the aequorin- and ECL-labeled probes react with a common capture probe binding site. In one such case the ECL-labeled indicator probe is held constant at 0.4 nmol/l, and in contrast the aequorin-labeled probe varied in a range from 0.1–10 nmol/l. In another case the aequorin-probe concentration is held constant at 1 nmol/l, while the ECL-probe concentration is varied in the range 0.4–40 nmol/l.

To enable direct comparison, primary data obtained from this experiment were normalized: the ECL-signal relative to 40 nmol/l (=large excess=100%), the aequorin-signal relative to 10 nmol/l (=100%). The relative changes which occurred after reaction of the different concentrations of the capture probes with a certain mixture of indicator probe were determined and then plotted graphically against the variable indicator probe concentration.

b. Results

The results of the determinations are shown in FIGS. 5 and 6. For identical hybridization sequences, it is to be expected that the intercept point of the curves is at exactly the point where the concentration of the probe which was held constant corresponds to the concentration of the probe whose concentration was not varied (at approximately 50%). If the concentration of the aequorin-labeled probe is set at 1 nmol/l and the concentration of the Ru$^{2+}$(bipy)$_3$-labeled probe varied then an intercept is obtained for the curves at approx. 0.8 nmol/l, i.e. 0.8 nmol/l Ru$^{2+}$(bipy)$_3$-labeled probes are equi-efficient to 1.0 nmol/l aequorin-labeled probe which reflects the molar mass effect (aequorin: 22000 Da, Ru$^{2+}$(bipy)$_3$ <1000 Da). Conversely, when one varies the aequorin-labeled probes an intercept of approx. 2 nmol/l results, i.e. 2 nmol/l are equi-efficient to 0.4 nmol/l RU2–(bipy)$_3$-labeled probe. These data which have been extrapolated from mean value data show that the rate of hybridization with both indicator probes, despite the significant molar mass differences, are very similar and the differences agree well with theoretically predicted values, whereby the principle suitability of duel labeled detection in accord with this invention for competitive qPCR on the basis of co-amplification using an internal standard is emphasized. This is further confirmed by the rest-activity of a labeled probe when the others are present in a maximal excess. This amounts to 4% when the concentration of the aequorin-labeled probe is held constant at 1 nmol/l and 14% when the concentration of the Ru$^{2+}$(bipy)$_3$-labeled probe is held constant at 0.4 nmol/l. This reflects the relative excess of the other respective probe of 40:1 in the first case and 25:1 in the latter case very well, the molar mass effect increasing the amount in favor of the expected tendency (i.e. kinetic advantage of Ru$^{2+}$(bipy)$_3$-labeled probes amplifies the effect of the concentration excess of these probes via the aequorin-labeled probes in the first case or reduces the effect of the concentration excess of the aequorin-labeled probes in the latter case).

EXAMPLE 4
Quantitative Determination of a Nucleic Acid Sample preparation and PCR-amplification If necessary, a raw sample is processed in such a manner that the nucleic acids are present in accessible form (e.g. lysis of cells etc.). The nucleic acids can also, if necessary, be amplified according to EP-B-0 201 184 (polymerase chain reaction). In accord with EP 0 420 260, biotin is incorporated using labeled primers.

Denaturing

10 µl of this reaction mixture are denatured by 40 µl of denaturing solution (composition 0.05 M sodium hydroxide solution, 0.15 M sodium chloride solution).

Hybridization

Finally two types of probe 2 are added of which one is ruthenium labeled (preferably the analyte-specific probe) and the other aequorin labeled (preferably the standard specific probe). The probes are dissolved in a hybridization solution composed of phosphate buffer, pH 6.5, sodium chloride and bovine albumin. 200 µl of the reaction mixture previously produced are added to the hybridization solution. The reaction mixture is incubated at 37° C. for 20 minutes.

Binding to Magnetic Beads

50 µl of magnetic streptavidin bead solution (from Elecsys® TSH-Immunoassay, Boehringer Mannheim GmbH, Cat. No. 1731459) (720 µg/ml) are added to the reaction mixture. The reaction mixture is incubated for 20 minutes at 37° C.

Measurement

150 µl of the reaction solution obtained are taken up in the device shown in FIG. 1 into the measuring cell. The electrochemiluminescence signal is measured first of all and then the aequorin signal is measured as described in example 1.

LIST OF REFERENCE NUMERALS (1) Conditioning solution for the measuring cell
(2) Cleaning solution for the measuring cell
(3) Calcium chloride-containing trigger solution
(4) Incubator
(5) Primary sample rotor
(6) Movable pipetter
(7) Photomultiplier
(8) Movable magnet
(9) Reference electrode
(10) Working electrode
(11) Counter electrode
(12) Pump
(13) Measuring cell
(14) Switching unit for a piston pump

---

What is claimed is:

1. A method for determining an analyte nucleic acid in a sample, comprising
    (a) amplifying (1) an analyte nucleic acid to be determined and (2) a known amount of a standard nucleic acid in a sample, to produce amplification products,
    (b) combining the amplification products from said amplifying step (a) with an analyte nucleic acid-specific probe and a standard nucleic acid-specific probe, wherein the analyte nucleic acid-specific probe is labeled with a first labeling group and the standard nucleic acid-specific probe is labeled with a second labeling group, wherein one of the first and second labeling groups is capable of electrically generating an electromagnetic signal and the other of the first and second labeling groups is capable of chemically generating an electromagnetic signal, to bind (1) the analyte nucleic acid-specific probe to the analyte nucleic acid and (2) the standard nucleic acid-specific probe to the standard nucleic acid,
    (c) generating electromagnetic signals from each of the first and second labeling groups, and
    (d) determining the electromagnetic signals generated in said generating step (c) and correlating the determined electromagnetic signals to the presence or amount of the analyte nucleic acid.

2. The method of claim 1, wherein the analyte nucleic acid is of viral or bacterial origin.

3. The method of claim 1, further comprising, between steps (b) and (c), separating the bound probes and any unbound probes.

4. The method of claim 1, wherein, in said generating step (c), the electromagnetic signals from each of the first and second labeling groups are generated simultaneously.

5. The method of claim 1, wherein, in said generating step (c), the electromagnetic signals from each of the first and second labeling groups are generated consecutively.

6. The method of claim 1, wherein, in said generating step (c), the electrically-generated electromagnetic signal is generated before the chemically-generated electromagnetic signal.

7. The method of claim 1, wherein the each of the first and second labeling groups are luminescent labeling groups.

8. The method of claim 7, wherein the one of the first and second labeling groups comprises a metal complex which is capable of electrically generating an electromagnetic signal and the other of the first and second labeling groups comprises a photoprotein.

9. A method for determining an analyte in a sample, comprising the following steps:
    (a) incubating the sample containing the analyte to be determined with at least two probes, wherein said two probes are a first probe and a second probe, wherein at least the first probe is specific for the analyte to be determined and the second probe is specific for a substance in the sample that differs in structure from the analyte,
    wherein one of the at least two probes is labeled with a first labeling group and another of the at least two probes is labeled with a second labeling group which is different than the first labeling group,
    to bind the at least one analyte-specific probe to its corresponding analyte to produce a bound product,
    (b) separating non-analyte bound first probe from the bound product,
    (c) generating different electromagnetic signals from each of the first and second labeling groups, wherein one of the first and second labeling groups electrically generates an electromagnetic signal and the other of the first and second labeling groups chemically generates an electromagnetic signal, and
    (d) determining the electromagnetic signals generated in said generating step (c) and correlating the determined electromagnetic signals to the presence or amount of the analyte.

10. The method of claim 9, wherein the sample further contains an additional component, and another of the at least two probes is specific for the additional component.

11. The method of claim 10, wherein the additional component comprises a known amount of a standard analyte.

12. The method of claim 9, wherein the analyte is selected from the group consisting of an antigen, an antibody, a cell and a nucleic acid.

13. The method of claim 12, wherein the analyte is a nucleic acid.

14. The method of claim 13, wherein the nucleic acid is of viral or bacterial origin.

15. The method of claim 9, wherein the first and second labeling groups are initially unable to generate detectable electromagnetic signals, and the method further comprises, between steps (a) and (b), or between steps (b) and (c), reacting the first and second labeling groups with reagents to enable the first and second labeling groups to generate detectable electromagnetic signals in step (c).

16. The method of claim 15, wherein the first and second labeling groups are each independently selected from the group consisting of haptens and vitamins.

17. The method of claim 9, wherein, in said generating step (c), the electromagnetic signals from each of the labels are generated simultaneously.

18. The method of claim 9, wherein, in said generating step (c), the electromagnetic signals from each of the labels are generated consecutively.

19. The method of claim 9, wherein, in said generating step (c), the electrically-generated electromagnetic signal is generated before the chemically-generated electromagnetic signal.

20. The method of claim 9, wherein the first and second labeling groups are luminescent labeling groups.

21. The method of claim 20, wherein one of the first and second labeling groups comprises a metal complex which is capable of electrically generating an electromagnetic signal and the other of first and second labeling groups comprises a photoprotein.

22. A method for determining an analyte in a sample, comprising the following steps:
  (a) incubating the sample, containing
    (1) the analyte to be determined and
    (2) a substance which differs in structure from the analyte, with at least two probes,
    wherein the at least two probes comprise a first probe and a second probe wherein the first probe is specific for the analyte to be determined and the second probe is specific for the substance which differs in structure from the analyte, to bind at least the first probe to the analyte to produce a bound product,
    wherein the first probe is labeled with a first labeling group and the second probe is labeled with a second labeling group, wherein one of the first and second labeling groups is capable of electrically generating an electromagnetic signal and the other of the first and second labeling groups is capable of chemically generating an electromagnetic signal,
  (b) separating the bound product from any unbound first probes,
  (c) thereafter generating electromagnetic signals from each of the first and second labeling groups, and
  (d) determining the electromagnetic signals generated in said generating step (c) and correlating the determined electromagnetic signals to the presence or amount of the analyte.

23. The method of claim 22, wherein the analyte is selected from the group consisting of an antigen, an antibody, a cell and a nucleic acid.

24. The method of claim 23, wherein the analyte is a nucleic acid.

25. The method of claim 24, wherein the nucleic acid is of viral or bacterial origin.

26. The method of claim 22, wherein, in said generating step (c), the electromagnetic signals from each of the labels are generated simultaneously.

27. The method of claim 22, wherein, in said generating step (c), the electromagnetic signals from each of the labels are generated simultaneously.

28. The method of claim 22, wherein, in said generating step (c), the electromagnetic signals from each of the labels are generated consecutively.

29. The method of claim 22, wherein, in said generating step (c), the electrically-generated electromagnetic signal is generated before the chemically-generated electromagnetic signal.

30. The method of claim 22, wherein the labels are luminescent labels.

31. The method of claim 30, wherein the one of the at least two probes has a label comprising a metal complex which is capable of electrically generating an electromagnetic signal and the another of the at least two probes has a label comprising a photoprotein.

32. The method of claim 22, wherein a known amount of standard analyte is used in said incubating step (a).

* * * * *